(12) United States Patent
Zhang et al.

(10) Patent No.: US 7,214,813 B2
(45) Date of Patent: May 8, 2007

(54) PREPARATION OF CHIRAL CYCLIC AMINO ACIDS AND DERIVATIVES

(75) Inventors: Xumu Zhang, State College, PA (US); Wenjun Tang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 362 days.

(21) Appl. No.: 10/855,103

(22) Filed: May 27, 2004

(65) Prior Publication Data

US 2004/0242889 A1    Dec. 2, 2004

Related U.S. Application Data

(60) Provisional application No. 60/474,535, filed on May 30, 2003.

(51) Int. Cl.
| | |
|---|---|
| C07C 69/74 | (2006.01) |
| C07C 271/62 | (2006.01) |
| C07C 271/00 | (2006.01) |
| C07C 205/02 | (2006.01) |
| C07C 229/46 | (2006.01) |

(52) U.S. Cl. ............ 560/128; 560/115; 560/121; 560/125; 560/155; 560/169

(58) Field of Classification Search ............ None
See application file for complete search history.

(56) References Cited

FOREIGN PATENT DOCUMENTS

WO    WO 99/59721   *   11/1999

OTHER PUBLICATIONS

Dobbs et al. Angew. Chem. Int. Ed. 2000, 39, pp. 1992-1995.*
Greene et al. "Protective Groups In Organic Synthesis" 2nd Edition, 1991, John Wiley & Sons Inc. pp. 229, 230, 318, 319, 327, 328, 335, 336.*
Heller et al. Tetrahedron: Asymmetry, 2002, vol. 13, pp. 2735-2741.*

* cited by examiner

*Primary Examiner*—Thurman Page
*Assistant Examiner*—Valenrod Yevgeny
(74) *Attorney, Agent, or Firm*—Ohlandt, Greeley, Ruggiero & Perle, L.L.P.

(57) ABSTRACT

Cyclic β-(acylamino)acrylate derivatives were hydrogenated using Ru-chiral phosphine ligand catalysts and thereafter converted to the corresponding cyclic β-aminoacids in high yield and enantioselectivity according to the reaction scheme:

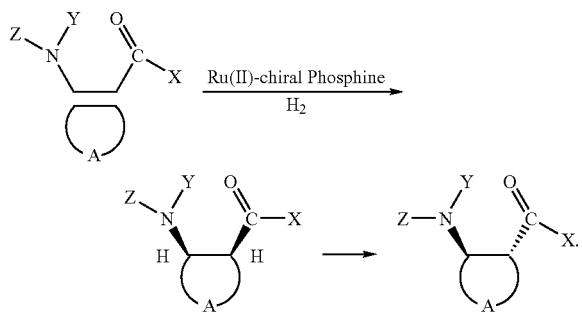

18 Claims, No Drawings

PREPARATION OF CHIRAL CYCLIC AMINO ACIDS AND DERIVATIVES

This application claims priority from U.S. Provisional Application Ser. No. 60/474,535, filed May 30, 2003.

The United States Government has certain license rights to this invention resulting from the development thereof under National Institute of Health Grant Number 5R01 GM 58832-04.

BACKGROUND OF THE INVENTION

1. Field of the Invention

The present invention relates to the preparation of enantiomerically enriched compounds using asymmetric catalysis. More particularly, the invention relates to the development of efficient catalysts and procedures for hydrogenation of tetra-substituted olefins of cyclic β-(acylamino)-acrylates to prepare enantiomerically enriched beta aminoacids.

2. Description of the Related Art

Enantiomerically pure β-amino acids and their derivatives are key structural elements of many natural products and drugs. They are also important chiral building blocks for the synthesis of β-peptides for biomedical research. For instance, trans-aminocyclopentanecarboxylic acid (1, trans-ACPC, FIG. 1) and trans-4-aminopyrrolidine-3-carboxylic acid (2, trans-APC) have been successfully used by Gellman et al. for constructing β-peptide antibiotics, while (1R,2S)-cis-aminocyclopentane-carboxylic acid (3, cispentacin) itself is a strong antifungal antibiotic.

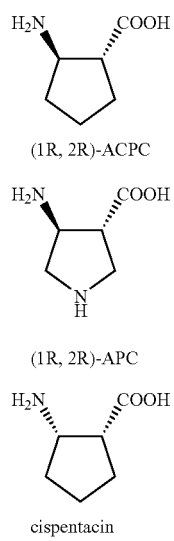

(1R, 2R)-ACPC (1R, 2R)-APC cispentacin

Although some stoichiometric asymmetric synthesis or resolution methods of chiral cyclic β-amino acids and their derivatives have been reported [Berkessel, A.; Glaubitz, K.; Lex, J. *Eur. J. Org. Chem.* 2002, 2948. Yokota, Y.; Cortez, G. S.; Romo, D. *Tetrahedron* 2002, 58, 7075. Leplae, P. R.; Umezawa, N.; Lee, H.-S.; Gellman, S. H. *J. Org. Chem.* 2001, 66, 5629. Davies, S. G.; Ichihara, O.; Walters, I. A. S. *Synlett* 1993, 461. Yamazaki, T.; Zhu, Y.-F.; Probstl, A.; Chadha, R. K.; Goodman, M. *J. Org. Chem.* 1991, 56, 6644.], development of new, efficient, and catalytic asymmetric synthetic methods remains an important goal.

Although great success has been achieved in asymmetric hydrogenation of tri-substituted functionalized olefins, hydrogenation of tetra-substituted olefins is generally more difficult and much fewer successful results have been reported [Blaser, H.-U.; Spindler, Malan, C.; Pugin, B.; Spindler, F.; Steiner, H.; Studer, M. *Adv. Synth. Catal.* 2003, 345, 103].

Bruneau et al [Dupau, P.; Bruneau, C.; Dixneuf, P. H. *Adv. Synth. Catal.* 2001, 343, 331] and Rautenstrauch et al [Dobbs, D. A.; Vanhessche, K. P. M.; Brazi, E.; Rautenstrauch, V.; Lenoir, J.-Y.; Genet, J.-P.; Wiles, J.; Bergens, S. H. *Angew. Chem. Int. Ed.* 2000, 39, 1992] have reported hydrogenation of tetrasubstituted enamides and a vinylogous β-oxoester by employing Ru catalysts.

While many excellent chiral catalytic systems have been developed for hydrogenation of trisubstituted olefins of acyclic β-(acylamino)acrylates to make beta amino acids, enantioselective hydrogenation of tetra-substituted olefins of cyclic or acyclic β-(acylamino)acrylates remains an unexplored area. Accordingly, development of efficient catalysts and procedures for hydrogenation of tetra-substituted olefins of cyclic or acyclic β-(acylamino)acrylates for making beta aminoacids is a primary object of the present invention.

SUMMARY OF THE INVENTION

In broad concept, the present invention provides a method of preparing cis-hydrogenated cyclic and acyclic β-acylaminocarbonyl derivatives from the corresponding tetrasubstituted olefins.

In one aspect, the present invention provides a method of preparing an enantiomerically enriched cis-cyclic β-acylaminocarbonyl derivative represented by the formula:

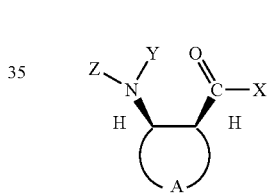

wherein:

X is can be alkyl, aryl, substituted alkyl, substituted aryl, heteroaryl, hydrogen, hydroxy, alkoxy, aryloxy, OCR₂OR, OSiR₃, amino, alkylamino, arylamino, dialkylamino, diarylamino, or alkylarylamino;

Y and Z can independently be hydrogen, alkyl, aryl, substituted alkyl, substituted aryl, heteroaryl, t-BuOCO (BOC), Fmoc peptide protecting group, PhCH₂OCO (CBZ), acyl or COOR, with the proviso that at least one of Y and Z is t-BuOCO (BOC), Fmoc peptide protecting group, PhCH₂OCO (CBZ), acyl or COOR;

A can be alkylene, substituted alkylene, alkylene of formula (CH₂)ₙ wherein n is an integer from 1–10, arylene, substituted arylene, heteroarylene, (CH₂)ₗarylene(CH₂)ₘ, (CH₂)ₗNR'(CH₂)ₘ, (CH₂)ₗO(CH₂)ₘ, (CH₂)ₗS(CH₂)ₘ, (CH₂)ₗCO(CH₂)ₘ or (CH₂)ₗC(=CH₂)(CH₂)ₘ;

wherein R' can be hydrogen, alkyl, substituted alkyl, aryl, substituted aryl, acyl, COOR, t-BuOCO (BOC), Fmoc peptide protecting group or PhCH₂OCO (CBZ);

wherein R can be hydrogen, alkyl, substituted alkyl, aryl or substituted aryl; and wherein each l and m is independently 0, 1, 2 or 3;

the method including the step of:

contacting hydrogen and a cyclic β-(acylamino)acrylate derivative represented by the formula:

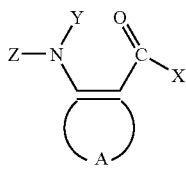

wherein the step of contacting is carried out in the presence of a Ru(II)-chiral phosphine ligand catalyst at a temperature, pressure and for a length of time sufficient to produce the enantiomerically enriched cis-cyclic β-acylaminocarbonyl derivative, wherein X, Y, Z, A, R, R', l, m, and n have the same meaning as before.

In another aspect, the present invention provides a method of preparing an enantiomerically enriched cis-hydrogenated acyclic, tetrasubstituted β-acylaminocarbonyl derivative represented by the formula:

YZN-CHR¹—CHR²C(O)X wherein:

R¹ and R² can independently be alkyl, aryl, substituted alkyl or substituted aryl;

X can be alkyl, aryl, substituted alkyl, substituted aryl, heteroaryl, hydrogen, hydroxy, alkoxy, aryloxy, $OCR_2OR$, $OSiR_3$, amino, alkylamino, arylamino, dialkylamino, diarylamino or alkylarylamino;

Y and Z can independently be hydrogen, alkyl, aryl, substituted alkyl, substituted aryl, heteroaryl, t-BuOCO (BOC), Fmoc peptide protecting group, $PhCH_2OCO$ (CBZ), acyl or COOR, with the proviso that at least one of Y and Z is t-BuOCO (BOC), Fmoc peptide protecting group, $PhCH_2OCO$ (CBZ), acyl or COOR;

wherein R' can be hydrogen, alkyl, substituted alkyl, aryl, substituted aryl, acyl, COOR, t-BuOCO (BOC), Fmoc peptide protecting group or $PhCH_2OCO$ (CBZ);

wherein R can be hydrogen, alkyl, substituted alkyl, aryl or substituted aryl; and wherein each l and m is independently 0, 1, 2 or 3;

the method including the step of:

contacting hydrogen and an acyclic, tetrasubstituted α-(acylamino)acrylate derivative represented by the formula:

YZN-CR¹=CR²C(O)X wherein the step of contacting is carried out in the presence of a Ru(II)-chiral phosphine ligand catalyst at a temperature, pressure and for a length of time sufficient to produce the enantiomerically enriched cis-hydrogenated acyclic, tetrasubstituted β-acylaminocarbonyl derivative, wherein X, Y, Z, A, R, R', l, m, and n have the same meaning as before.

The present invention provides efficient catalysts procedures for hydrogenation of tetra-substituted olefins of cyclic or acyclic β-(acylamino)-acrylates to produce β-acylaminocarbonyl derivative, which can be transformed to beta aminoacids in high yield and enantioselectivity.

DETAILED DESCRIPTION OF THE INVENTION

The present invention provides a method of preparing enantiomerically enriched cyclic β-amino acids. The method includes the reaction of a cyclic or acyclic β-(acylamino) acrylate in the presence of a Ru(II)-chiral phosphine ligand catalyst according to the following scheme (shown for the cyclic acrylate systems:

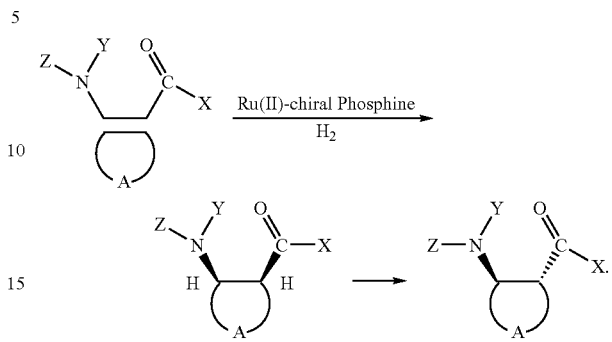

In a preferred embodiment of the method of present invention, X can be hydroxy, alkoxy, aryloxy, $OCR_2OR$, $OSiR_3$, amino, alkylamino, arylamino, dialkylamino, diarylamino, or alkylarylamino.

The method further includes the step of contacting the enantiomerically enriched cis-cyclic β-acylaminocarbonyl derivative and water in the presence of a catalyst under reaction conditions sufficient to convert the enantiomerically enriched cis-cyclic β-acylaminocarbonyl derivative to an enantiomerically enriched cis-cyclic β-aminoacid derivative, which can be further contacted with a base under reaction conditions sufficient to convert the cis-cyclic β-aminoacid derivative to a trans-cyclic β-aminoacid derivative through a cis-trans isomerization at the carbon alpha to the carbonyl.

The cis-cyclic β-acylaminocarbonyl derivative can also be isomerized by contacting the enantiomerically enriched cis-cyclic β-acylaminocarbonyl derivative and a base under reaction conditions sufficient to convert the enantiomerically enriched cis-cyclic β-acylaminocarbonyl derivative to an enantiomerically enriched trans-cyclic β-acylaminocarbonyl derivative represented by the formula:

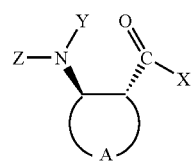

wherein X, Y, Z, A, R, R', l, m, and n have the same meaning as before.

In the preferred embodiment when X is hydroxy, alkoxy, aryloxy, $OCR_2OR$, $OSiR_3$, amino, alkylamino, arylamino, dialkylamino, diarylamino, or alkylarylamino, the trans-cyclic β-acylaminocarbonyl derivative can be hydrolyzed with water in the presence of a catalyst under reaction conditions sufficient to convert the enantiomerically enriched trans-cyclic β-acylaminocarbonyl derivative directly to the trans-cyclic β-aminoacid derivative.

Using the above approaches, a wide variety of cis- and trans-cyclic β-aminoacids were prepared, including the enantiomerically enriched trans-cyclic β-aminoacids represented by the formula:

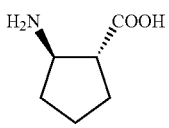

(1R, 2R)-ACPC and

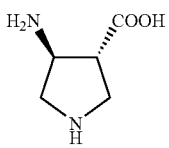

(1R, 2R)-APC and the enantiomerically enriched cis-cyclic α-aminoacid derivative represented by the formula:

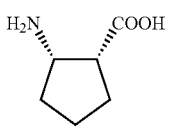

cispentacin

The method of the present invention is not limited to the preparation of cyclic β-acylaminocarbonyl derivatives. The present method is also useful in the preparation of acyclic β-acylaminocarbonyl derivatives and the corresponding carboxylic acids via hydrolysis of the group —COX to a —COOH group.

The catalysts useful in the present invention can vary widely. The catalyst can be any Ru(II)-chiral phosphine catalyst capable of asymmetric hydrogenation of cyclic β-(acylamino)acrylates for producing the cyclic β-aminoacids.

Suitable chiral monophoshine and bisphosphine compounds include MonoPhos, MOP, ChiraPhos, SkewPhos, BINAP, DIOP, DIOP*, MeO-BIPHEP, Me-BIPHEP, DuPhos, BPE, JosiPhos, Ferrotane, DeguPhos, MeO-BIPHEP, SEGPhos, H$_8$BINAP, BICP, PennPhos, KetalPhos, f-KetalPhos, BINAPHANE, f-BINAPHANE, TangPhos, DuanPhos, BINAPhine, o-BIPHEP, CnTunaPhos (n=1–6), RoPhos, MalPhos, WalPhos, MandyPhos, TaniaPhos, BITIANP, BITIOP, and PhanePhos.

Ligands that are suitable for use in the present invention are described in detail in W. Tang, X. Zhang, New Chiral Phosphorus Ligands for Enantioselective Hydrogenation, *Chemical Reviews*, Vol. 103, No. 8, 2003. Several of these ligands (including TunaPhos, DIOP*, BINAPHANE, f-BINAPHANE) are commercially available from ChiralQuest, State College, Pa.

Preparation of the others have been described in either the literature, published patent documents or both. Preparation of these ligands is relatively simple and can be carried out by those skilled in the art of asymmetric synthesis and catalysis and are familiar with the published procedures. The manufacture of some of these ligands is described in the following U.S. Pat. Nos. 5,202,493; 5,329,015; 5,767,276; 5,936,127; 6,037,500; 6,207,868; 6,255,493; 6,278,024; 6,337,406; 6,380,392; 6,380,416; 6,399,878; 6,451,727; 6,476,233; 6,521,769; 6,525,210; and 6,534,657 which are hereby incorporated herein by reference as fully set forth.

Below are the structures of some of the chiral ligands used in the examples:

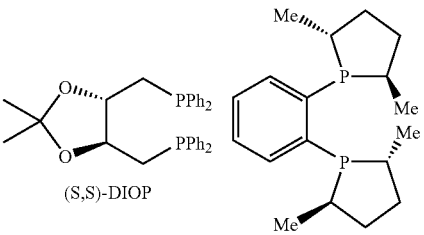

(S,S)-DIOP (R,R)-Me-DuPhos

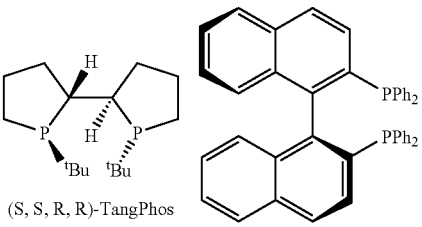

(S, S, R, R)-TangPhos (S)-BINAP

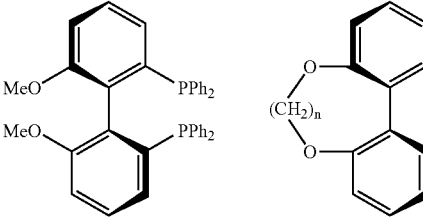

(S)-BIPHEP (S)-Cn-TunaPhos
n = 1–6

The preferred hydrogenation catalysts are Ru(II)-chiral phosphine ligand catalysts. The chiral phosphine ligand in the Ru(II)-chiral phosphine ligand catalyst can be a chiral monophoshine or bisphosphine compound. Examples of the Ru(II)-chiral phosphine ligand catalyst based on the above chiral monophoshine or bisphosphine compounds include RuHX(L)$_2$(diphosphine), RuX$_2$(L)$_2$(diphosphine), Ru(aryl)X$_2$ (monophosphine)$_2$, Ru(arene)X$_2$(diphosphine), Ru(aryl)X$_2$(diphosphine), Ru(R"COO)$_2$(diphosphine), RuCl$_2$(=CHR")(monophosphine)$_2$, [NH$_2$R"$_2$][{RuX(diphosphine)}$_2$(μ-X)$_3$], RuH(COD)(diphosphine)X, RuX$_2$(diphosphine), and Ru(methallyl)$_2$(diphosphine). The R" can be alkyl and aryl; and wherein L is a solvent or alkene, and X is a counteranion, such as, halogen, BF$_4^-$, B(Ar)$_4^-$ wherein Ar is fluorophenyl or 3,5-di-trifluoromethyl-1-phenyl, ClO$_4^-$, SbF$_6^-$, PF$_6^-$, CF$_3$SO$_3^-$, R"COO$^-$ or a mixture thereof.

The precursors from which the Ru(II)-chiral phosphine ligand catalyst can be prepared include Ru(COD)(COT), Ru(COD)(COT)X, RuX$_2$(cymen), Ru(COD)$_n$, RuCl$_2$(COD), Ru(COD)$_2$X, Ru(ArH)Cl$_2$, and Ru(COD)(methallyl)$_2$.

The hydrogenation can be carried out by methods known in the art, such as, using hydrogen under pressure, at ambient or at superambient temperatures for a period of time from about several minutes to several hours.

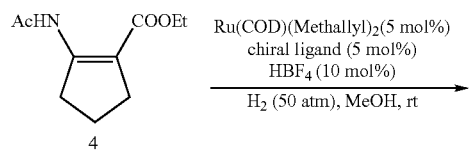

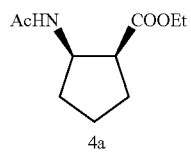

In one approach, tetrasubstituted olefin 4 is used as a typical substrate. The Ru catalysts were prepared in situ by protonation of a mixture of Ru(COD)(methallyl)$_2$ and a chiral bisphosphorous ligand with two equivalent of HBF$_4$·Me$_2$O. After evaporation of solvent, the residue was directly used for hydrogenation. The hydrogenations were performed at rt under 50 atm of H$_2$ pressure in MeOH.

As shown in Table 1, different chiral ligands exhibited dramatically different enantioselectivities. While DIOP, DuPhos, and TangPhos gave only moderate enantioselectivities, chiral biaryl ligands such as MeO-BIPHEP and BINAP provided 99% ee's.

To test the effect of the dihedral angle of chiral biaryl ligand on enantioselectivity of the reaction, a set of TunaPhos ligands with different dihedral angles were employed [Wu, S.; Wang, W.; Tang, W.; Lin, M.; Zhang, X. Org. Lett. 2002, 4, 4495. Zhang, Z.; Qian, H.; Longmire, J.; Zhang, X. J. Org. Chem. 2000, 65, 6223]. Except C1-TunaPhos and C6-TunaPhos that provided slightly lower ee's, other TunaPhos ligands showed comparably high enantioselectivities. The preparation method of the Ru catalysts is important for the high reactivity. When a different Ru catalyst precursor such as [NH$_2$Me$_2$][{RuCl((S)—C3-TunaPhos)}$_2$(μ-Cl)$_3$] was applied for hydrogenation under identical conditions, a lower conversion (80%) was obtained although the high enantioselectivity was maintained. Alcoholic solvents are beneficial for the reactivity.

C3-TunaPhos is used as the ligand for Ru-catalyzed asymmetric hydrogenation of a series of cyclic β-(acylamino)acrylates. As shown in Table 2, over 99% ee was obtained in hydrogenation of 2-acetylamino-cyclopent-1-enecarboxylic acid methyl ester 5. Excellent enantioselectivity (98% ee) was also achieved in hydrogenation of Boc-protected substrate 6. The chiral cis product 6a was used as a synthon for the peptide is.

TABLE 1

Ru-catalyzed hydrogenation of 2-acetylamino-cyclopent-1-enecarboxylic acid ethyl ester

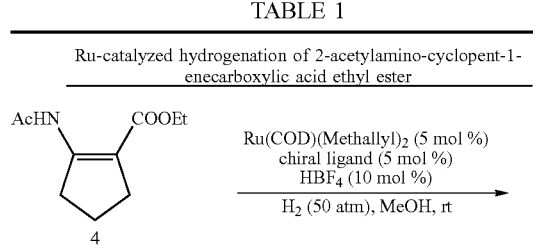

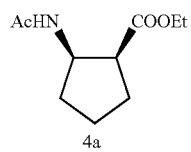

| Entry[a] | chiral P* ligands | conv.(%) | % ee (config) |
|---|---|---|---|
| 1 | (S, S)-DIOP | 91 | 34 (2S, 3R) |
| 2 | (R, R)-Me-DuPhos | 100 | 69 (2R, 3S) |
| 3 | (S, S, R, R)-TangPhos | 100 | 57 (2R, 3S) |
| 4 | (S)-BINAP | 100 | 99 (2S, 3R) |
| 5 | (S)-MeO-BIPHEP | 100 | 99 (2S, 3R) |
| 6 | (S)-C1-TunaPhos | 100 | 98 (2S, 3R) |
| 7 | (S)-C2-TunaPhos | 100 | 99 (2S, 3R) |
| 8 | (S)-C3-TunaPhos | 100 | 99 (2S, 3R) |
| 9 | (S)-C4-TunaPhos | 100 | 99 (2S, 3R) |
| 10 | (S)-C5-TunaPhos | 100 | 99 (2S, 3R) |
| 11 | (S)-C6-TunaPhos | 100 | 97 (2S, 3R) |

[a]For detailed procedure of catalyst preparation, see supporting information given below in the Examples.
Ru:P*:HBF4:substrate = 1:1:2:20, The hydrogenations were performed at rt under 50 atm of H$_2$ pressure in MeOH for 18 h.

TABLE 2

Hydrogenation of cyclic or acyclic β-(acylamino)acrylates with a Ru-(S)-C3-TunaPhos catalyst

| entry[a] | substrate | product | ee (%)[b] |
|---|---|---|---|
| 1 | (4) | (4a) | 99 |
| 2 | (5) | (5a) | >99 |
| 3 | (6) | (6a) | 98[c] |
| 4 | (7) | (7a) | 95 |
| 5 | (8) | (8a) | 92 |

TABLE 2-continued

Hydrogenation of cyclic or acyclic β-(acylamino)acrylates with a Ru-(S)-C3-TunaPhos catalyst

| entry[a] | substrate | product | ee (%)[b] |
|---|---|---|---|
| 6 | (9) AcHN-COOMe (cycloheptenyl) | (9a) | 80 |
| 7 | (10) AcHN-COOMe (cyclooctenyl) | (10a) | 44[d] |
| 8 | (11) AcHN-COOEt | (11a) | 72 |

[a]For detailed procedure of catalyst preparation, see supporting information given below in the Examples.
Note that the ratio Ru:(S)-C3-TunaPhos:HBF4:substrate = 1:1:2:20. The hydrogenations were carried at rt under 50 atm of H$_2$ pressure in EtOH for 18 h.
[b]The absolute configuration of entry 3 is determined as (1S, 2R); the absolute configuration of entry 7 is not determined; the others are assigned by analogy according to optical rotations.
[c]The enantiomeric excesses are determined by chiral GC on a chiralselect 1000 or-γ-dex 225 column.

A heterocyclic β-(acylamino)acrylate 7 was also hydrogenated to give the cis product 7a in excellent enantioselectivity.

Hydrogenation of a cyclohexenyl substrate 8 provided the cis hydrogenation product in 92% ee. However, lower ee's were obtained in the hydrogenation of cycloheptenyl and cyclooctenyl substrates 9 and 10 under comparable hydrogenation conditions.

An acyclic β-(acylamino)acrylate 11 with a tetrasubstituted olefin was also hydrogenated and the product 11a was obtained in 72% ee.

Hydrogenation with other biaryl ligands such as BINAP, MeO-BIPHEP, C2-, C4-, and C5-TunaPhos also showed similar hydrogenation results.

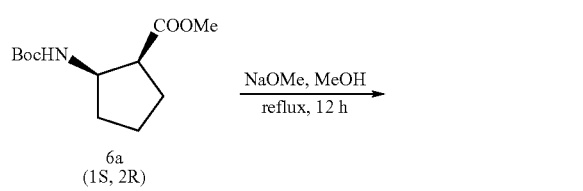

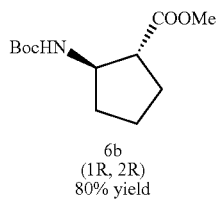

Synthetic utility of the chiral cis hydrogenation products is demonstrated for making trans cyclic β-amino acid derivatives, compound 6a was heated in a basic alcoholic solution to yield its trans epimer trans-(1R, 2R)-2-tert-butoxycarbonylamino-cyclopentanecarboxylic acid methyl ester (6b) in high yield.

Catalytic asymmetric synthesis of chiral cyclic β-amino acid derivatives and related compounds via asymmetric hydrogenation has been demonstrated. The Ru catalysts combined with several chiral phosphine ligands are found to be efficient for hydrogenation of tetrasubstituted olefins of cyclic β-(acylamino)acrylates and up to 99% ee's have been achieved.

The cyclic β-(acylamino)acrylates can be synthesized from their corresponding cyclic β-keto esters through amination and acylation in high yields. Since the hydrogenation substrates are easy to synthesize, this methodology can be practical for the synthesis of both cis, trans chiral cyclic β-amino acids and related compounds.

EXAMPLES

General Procedures:

All reactions and manipulations were performed in a nitrogen-filled glove box or using standard Schlenk techniques. THF and toluene were dried and distilled from sodium-benzophenone ketyl under nitrogen. Methylene chloride was distilled from CaH$_2$. Methanol was distilled from Mg under nitrogen. (R, R)-BDNPB was made a solution of 10 mg/ml in toluene before use. Column chromatography was performed using EM silica gel 60 (230–400 mesh). $^1$H, $^{13}$C and $^{31}$P NMR were recorded on Bruker WP-200, AM-300, and AMX-360 spectrometers. Chemical shifts were reported in ppm down field from tetramethylsilane with the solvent resonance as the internal standard. Optical rotation was obtained on a Perkin-Elmer 241 polarimeter. MS spectra were recorded on a KRATOS mass spectrometer MS 9/50 for LR-EI and HR-EI. GC analysis was carried on Hewlett-Packard 6890 gas chromatography using chiral capillary columns. HPLC analysis was carried on Waters™ 600 chromatography.

General Procedures for the Synthesis of β-(acylamino) Acrylates

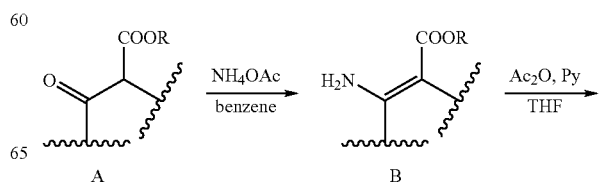

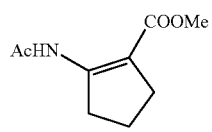

5

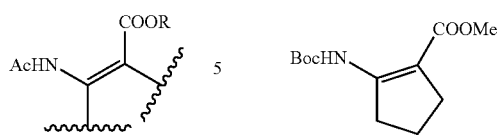

6

A mixture of β-keto ester A (100 mmol) and ammonium acetate (38.5 g, 500 mmol) in MeOH (250 mL) was stirred at room temperature until the starting material totally disappeared. The whole reaction mixture was then concentrated. The residue was redissolved in $CH_2Cl_2$ (200 mL). The resulting solid was filtered and washed with ample $CH_2Cl_2$. The combined $CH_2Cl_2$ was washed with water and brine, and then dried over sodium sulfate. The solution was concentrated under vacuum to give enamine B, which was used directly for the next step without further purifications.

A mixture of enamine B (100 mmol), pyridine (18.2 mL, 225 mmol), and acetic anhydride (55 mL, 582 mmol) was heated at reflux overnight. The mixture was concentrated under vacuum. The residue was treated with EtOAc (300 mL) and 1N HCl (200 mL). The aqueous layer was discarded. The organic phase was washed sequentially with 1N HCl (100 mL), water (100 mL), and brine. After dried over anhydrous sodium sulfate, the solution was concentrated and the residue was distilled under vacuum or recrystallized to give pure β-(acylamino) acrylate product in 50–70% yield. For the synthesis of 2-tert-butoxycarbonylamino-cyclopent-1-enecarboxylic acid ethyl ester, $(BOC)_2O$ was used instead of $Ac_2O$.

2-tert-Butoxycarbonylamino-cyclopent-1-enecarboxylic acid methyl ester (6): $^1H$ NMR (CDCl$_3$) 300 MHz δ 9.54 (s, 1H), 3.73 (s, 3H), 3.08 (t, 7.7 Hz, 2H), 2.49 (m, 2H), 1.87 (m, 2H), 1.47 (s, 9H); $^{13}C$ NMR (CDCl$_3$) 75 MHz δ 168.5, 156.2, 152.3, 105.2, 81.4, 51.3, 34.0, 28.9, 28.5, 21.4; MS (ESI): 242 (M$^+$+1); HRMS calcd for $C_{12}H_{20}NO_4$ 242.1392; found 242.1382.

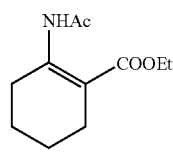

7

2-Acetylamino-cyclohex-1-enecarboxylic acid ethyl ester (7): $^1H$ NMR (CDCl$_3$) 360 MHz δ 11.56 (s, 1H), 4.15 (q, 7.1 Hz, 2H), 2.94 (m, 2H), 2.28 (m, 2H), 2.08 (s, 3H), 1.57 (m, 4H), 1.27 (t, 7.1 Hz, 3H); $^{13}C$ NMR (CDCl$_3$) 90 MHz δ 170.1, 168.8, 152.4, 104.5, 60.3, 28.6, 25.6, 24.3, 22.0, 21.9, 14.4; MS (ESI): 212 (M$^+$+1); HRMS calcd for $C_{11}H_{18}NO_3$ 212.1287; found 212.1299.

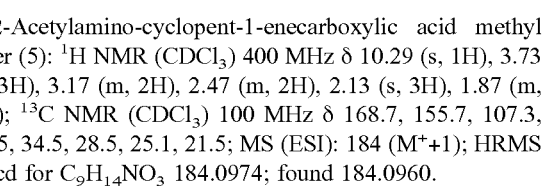

5

2-Acetylamino-cyclopent-1-enecarboxylic acid methyl ester (5): $^1H$ NMR (CDCl$_3$) 400 MHz δ 10.29 (s, 1H), 3.73 (s, 3H), 3.17 (m, 2H), 2.47 (m, 2H), 2.13 (s, 3H), 1.87 (m, 2H); $^{13}C$ NMR (CDCl$_3$) 100 MHz δ 168.7, 155.7, 107.3, 51.5, 34.5, 28.5, 25.1, 21.5; MS (ESI): 184 (M$^+$+1); HRMS calcd for $C_9H_{14}NO_3$ 184.0974; found 184.0960.

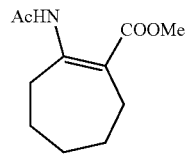

8

2-Acetylamino-cyclohept-1-enecarboxylic acid methyl ester (8): $^1H$ NMR (CDCl$_3$) 300 MHz δ 11.1 (s, 1H), 3.67 (s, 3H), 3.01 (m, 2H), 2.46 (m, 2H), 2.06 (s, 3H), 1.71 (m, 2H), 1.60 (m, 2H), 1.42 (m, 2H); $^{13}C$ NMR (CDCl$_3$) 75 MHz δ 170.4, 169.6, 158.6, 112.3, 51.9, 32.2, 30.2, 26.8, 26.2, 25.8, 24.8; MS (ESI): 212 (M$^+$+1); HRMS calcd for $C_{11}H_{18}NO_3$ 212.1287; found 212.1284.

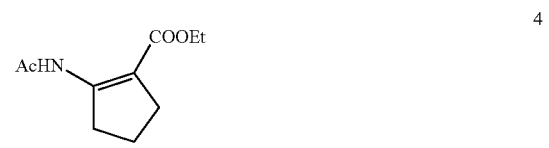

4

2-Acetylamino-cyclopent-1-enecarboxylic acid ethyl ester (4): $^1H$ NMR (CDCl$_3$) 360 MHz δ 10.29 (s, 1H), 4.17 (q, 7.1 Hz, 2H), 3.14 (m, 2H), 2.44 (m, 2H), 2.09 (s, 3H), 1.84 (m, 2H), 1.27 (t, 7.1 Hz, 3H); $^{13}C$ NMR (CDCl$_3$) 90 MHz δ 168.8, 168.3, 155.4, 107.6, 60.2, 34.5, 28.6, 25.0, 21.4, 14.7; MS (ESI): 198 (M$^+$+1); HRMS calcd for $C_{10}H_{16}NO_3$ 198.1130; found 198.1137.

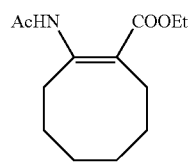

9

2-Acetylamino-cyclooct-1-enecarboxylic acid ethyl ester (9): $^1H$ NMR (CDCl$_3$) 360 MHz δ 11.71 (s, 1H), 4.17 (q, 7.1 Hz, 2H), 3.04 (m, 2H), 2.44 (m, 2H), 2.10 (s, 3H), 1.76 (m, 2H), 1.46 (m, 6H), 1.28 (t, 7.1 Hz, 3H); $^{13}C$ NMR (CDCl$_3$) 90 MHz δ 170.2, 168.5, 155.1, 107.7, 60.4, 30.2, 29.1, 27.6, 26.9, 26.5, 25.9, 25.4, 14.4; MS (ESI): 240 (M$^+$+1); HRMS calcd for $C_{13}H_{22}NO_3$ 240.1600; found 240.1597.

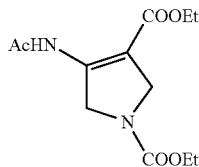

10

4-Acetylamino-2,5-dihydro-pyrrole-1,3-dicarboxylic acid diethyl ester (10): $^1$H NMR (CDCl$_3$) 360 MHz δ 10.09 (s, 1H), 4.83 (m, 2H), 4.16 (m, 6H), 2.14 (s, 3H), 1.28 (m, 6H); $^{13}$C NMR (CDCl$_3$) 90 MHz δ 168.4, 168.1, 165.8, 165.7, 154.9, 154.7, 148.1, 147.8, 102.5, 102.3, 61.5, 60.7, 53.6, 53.2, 49.3, 48.9, 24.3, 15.0, 14.5, 14.4 (two conformers); MS (ESI): 271 (M$^+$+1); HRMS calcd for C$_{12}$H$_{19}$N$_2$O$_5$ 271.1294; found 271.1315.

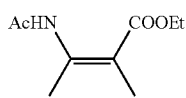

11

3-Acetylamino-2-methyl-but-2-enoic acid ethyl ester (11): $^1$H NMR (CDCl$_3$) 400 MHz δ 11.70 (s, 1H), 4.18 (q, 7.1 Hz, 2H), 2.40 (s, 3H), 2.10 (s, 3H), 1.82 (s, 3H), 1.30 (t, 7.1 Hz, 3H); $^{13}$C NMR (CDCl$_3$) 100 MHz δ 170.6, 169.4, 150.8, 103.5, 60.8, 25.9, 17.8, 14.7, 13.0; MS (ESI): 186 (M$^+$+1); HRMS calcd for C$_9$H$_{16}$NO$_3$ 186.1130; found 186.1142.

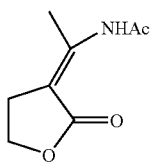

12

N-[1-(2-Oxo-dihydro-furan-3-ylidene)-ethyl]-acetamide (12): $^1$H NMR (CDCl$_3$) 360 MHz δ 10.80 (s, 1H), 4.33 (m, 2H), 2.89 (m, 2H), 2.37 (s, 3H), 2.10 (s, 3H); $^{13}$C NMR (CDCl$_3$) 90 MHz δ 173.0, 169.0, 149.2, 100.6, 65.8, 25.6, 25.3, 19.0;

General Hydrogenation Method

Ru(COD)(methallyl)$_2$ (3.2 mg, 10 μmol) and C3-TunaPhos (5.9 mg, 10 μmol) were dissolved in degassed dichloromethane (0.5 mL) in a Schlenk tube under N$_2$. The solution was cooled down to 0° C. and HBF$_4$.MeO (2.5 μL, 2.7 mg, 20 μmol) was slowed added. The resulting solution was then allowed to warm to rt and stirred for 0.5 h. The mixture was evaporated under vacuum, and the residue was dissolved in degassed dried EtOH (3 mL), and the solution was directly used for hydrogenation. To the catalyst solution was added substrate (0.2 mmol). The resulting mixture was transferred into an autoclave and charged with 50 atm of H$_2$ pressure. The autoclave was stirred at rt for 18 h.

The reaction solution was then evaporated and the residue was passed through a short silica gel plug to remove the catalyst. The resulting hydrogenation product was then directly analyzed by chiral GC (chiralselect 1000 or gama dex 225) to determine the enantiomeric excess.

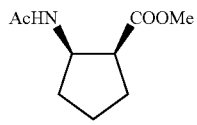

5a cis-(1S,2R)-2-Acetylamino-cyclopentanecarboxylic acid methyl ester (5a): >99% ee; [α]$^{20}_D$=+99.1° (c=1.8, CHCl$_3$); $^1$H NMR (CDCl$_3$) 400 MHz δ 6.16 (s, 1H), 4.47 (m, 1H), 3.66 (s, 3H), 2.99 (m, 1H), 1.97 (m, 3H), 1.93 (s, 3H), 1.80 (m, 1H), 1.64 (m, 2H); $^{13}$C NMR (CDCl$_3$) 90 MHz δ 175.6, 170.1, 52.5, 52.1, 46.7, 32.3, 28.6, 23.8, 22.6; MS (ESI): 186 (M$^+$+1); HRMS calcd for C$_9$H$_{16}$NO$_3$ 186.1130; found 186.1133. Chiral GC conditions: chiralselect 1000, 1 mL/min, 150° C. isothermal, 22.9 min (1R, 2S), 23.3 (1S, 2R).

cis-(1S,2R)-2-Acetylamino-cyclopentanecarboxylic acid ethyl ester (4a): 99% ee; [α]$^{20}_D$=+85.9° (c=0.9, CHCl$_3$); $^1$H NMR (CDCl$_3$) 360 MHz δ 6.14 (s, 1H), 4.45 (m, 1H), 4.09 (q, 7.1 Hz, 2H), 2.95 (m, 1H), 1.93 (m, 3H), 1.91 (s, 3H), 1.77 (m, 1H), 1.61 (m, 2H), 1.22 (t, 7.1 Hz, 3H); $^{13}$C NMR (CDCl$_3$) 100 MHz δ 175.1, 170.0, 60.9, 52.4, 46.8, 32.3, 28.6, 23.7, 22.6, 14.6; MS (ESI): 200 (M$^+$+1); HRMS calcd for C$_{10}$H$_{18}$NO$_3$ 200.1287; found 200.1306. Chiral GC conditions: chiralselect 1000, 1 mL/min, 160° C. isothermal, 24.5 min (1R, 2S), 25.4 (1S, 2R).

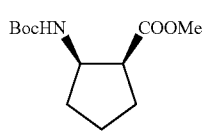

6a cis-(1S, 2R)-2-tert-Butoxycarbonylamino-cyclopentanecarboxylic acid ethyl ester (6a): 98% ee; [α]$^{20}_D$=+77.1° (c=1.8, CHCl$_3$); $^1$H NMR (CDCl$_3$) 400 MHz δ 4.93 (s, 1H), 4.22 (m, 1H), 3.68 (s, 3H), 3.01 (dd, 7.4 Hz, 15.0 Hz, 1H), 1.95 (m, 3H), 1.83 (m, 1H), 1.63 (m, 2H), 1.43 (s, 9H); $^{13}$C NMR (CDCl$_3$) 100 MHz δ 175.2, 155.7, 79.6, 54.2, 52.0, 47.2, 32.6, 28.7, 28.1, 22.6; MS (ESI): 244 (M$^+$+1); HRMS calcd for C$_{12}$H$_{22}$NO$_4$ 244.1549; found 244.1544. Chiral GC conditions: gama dex 225, 1 mL/min, 140° C. isothermal, 42.4 min (1R, 2S), 43.1 (1S, 2R).

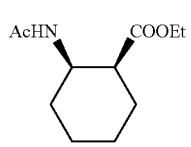

7a cis-(1S, 2R)-2-Acetylamino-cyclohexanecarboxylic acid ethyl ester (7a): 92% ee; $[\alpha]^{20}_D$=+50.0° (c=2.2, CHCl$_3$); $^1$H NMR (CDCl$_3$) 400 MHz δ 6.45 (b, 1H), 4.12 (m, 3H), 2.75 (m, 1H), 2.05 (m, 1H), 1.94 (s, 3H), 1.64 (m, 4H), 1.46 (m, 2H), 1.25 (t, 7.1 Hz, 3H), 1.24 (m, 1H); $^{13}$C NMR (CDCl$_3$) 100 MHz δ 174.6, 169.5, 60.8, 48.1, 44.7, 29.7, 27.6, 24.5, 24.0, 22.7, 14.6; MS (ESI): 214 (M$^+$+1); HRMS calcd for C$_{11}$H$_{20}$NO$_3$ 214.1443; found 214.1461. Chiral GC conditions: chiralselect 1000, 1 mL/min, 140° C. isothermal, 44.7 min (1R, 2S), 47.4 (1S, 2R).

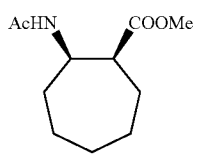

8a cis-(1S, 2R)-2-Acetylamino-cycloheptanecarboxylic acid methyl ester (8a): 80% ee; $[\alpha]^{20}_D$=+43.6° (c=1.7, CHCl$_3$); $^1$H NMR (CDCl$_3$) 360 MHz δ 6.19 (b, 1H), 4.21 (m, 1H), 3.67 (s, 3H), 2.87 (m, 1H), 1.91 (m, 4H), 1.78 (m, 3H), 1.40–1.70 (m, 6H); $^{13}$C NMR (CDCl$_3$) 90 MHz δ 175.3, 168.9, 51.7, 50.9, 47.7, 32.7, 27.3, 27.1, 25.2, 24.7, 23.7; MS (ESI): 214 (M$^+$+1); HRMS calcd for C$_{11}$H$_{20}$NO$_3$ 214.1443; found 214.1443. Chiral GC conditions: chiralselect 1000, 1 mL/min, 160° C. isothermal, 32.2 min (1R, 2S), 32.9 (1S, 2R).

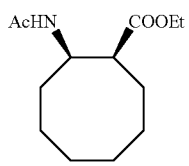

9a cis-2-Acetylamino-cyclooctanecarboxylic acid ethyl ester (absolute configuration not determined) (9a): 44% ee; $[\alpha]^{20}_D$=−17.9° (c=1.9, CHCl$_3$); $^1$H NMR (CDCl$_3$) 400 MHz δ 6.06 (d, 8.0 Hz, 1H), 4.43 (m, 1H), 4.15 (q, 7.1 Hz, 2H), 2.83 (m, 1H), 1.93 (m, 4H), 1.52–1.90 (m, 11H), 1.27 (t, 7.1 Hz, 3H); $^{13}$C NMR (CDCl$_3$) 100 MHz δ 175.2, 169.2, 61.0, 48.8, 47.1, 31.7, 27.5, 26.8, 26.2, 25.6, 25.0, 23.9, 14.6; MS (ESI): 242 (M$^+$+1); HRMS calcd for C$_{13}$H$_{24}$NO$_3$ 242.1756; found 242.1765. Chiral GC conditions: chiralselect 1000, 1 mL/min, 180° C. isothermal, 38.8 (large), 39.5 (small).

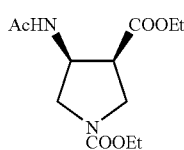

10a cis-(3S, 4R)-4-Acetylamino-pyrrolidine-1,3-dicarboxylic acid diethyl ester (10a): 95% ee; $[\alpha]^{20}_D$=+12.6° (c=0.9, CHCl$_3$); $^1$H NMR (CDCl$_3$) 360 MHz δ 6.43 (b, 1H), 4.74 (m, 1H), 4.11 (m, 4H), 3.60–3.85 (m, 3H), 3.37 (m, 1H), 3.18 (m, 1H), 1.94 (s, 6H), 1.21 (m, 6H); $^{13}$C NMR (CDCl$_3$) 90 MHz δ 171.7, 170.1, 155.2, 61.5, 51.0, 50.6, 50.0, 49.5, 47.4, 47.0, 46.3, 45.2, 23.3, 14.8, 14.2 (two conformers); MS (ESI): 273 (M$^+$+1); HRMS calcd for C$_{12}$H$_{21}$N$_2$O$_5$ 273.1450; found 273.1441. Chiral GC conditions: chiralselect 1000, 1 mL/min, 120° C. isothermal, 31.7 min (3S, 4R), 33.2 min (3R, 4S).

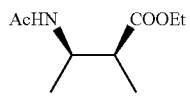

11a (2S, 3R)-3-Acetylamino-2-methyl-butyric acid ethyl ester (11a): 72% ee; $[\alpha]^{20}_D$=+23.6° (c=0.25, CHCl$_3$); $^1$H NMR (CDCl$_3$) 400 MHz δ 6.05 (b, 1H), 4.64 (m, 3H), 2.66 (m, 1H), 1.99 (s, 3H), 1.30 (t, 7.1 Hz, 3H), 1.19 (d, 7.2 Hz, 3H), 1.14 (d, 6.8 Hz, 3H); $^{13}$C NMR (CDCl$_3$) 100 MHz δ 174.7, 169.5, 61.0, 47.4, 44.3, 24.0, 16.9, 14.6, 14.1; MS (ESI): 188 (M$^+$+1); HRMS calcd for C$_9$H$_{18}$NO$_3$ 188.1287; found 188.1280. Chiral GC conditions: chiralselect 1000, 1 mL/min, 140° C. isothermal, 15.0 min (2R, 3S), 16.0 (2S, 3R).

Preparation of trans-(1R, 2R)-2-tert-butoxycarbonylamino-cyclopentanecarboxylic acid methyl ester and Determination of Absolute Configuration of Hydrogenation Product

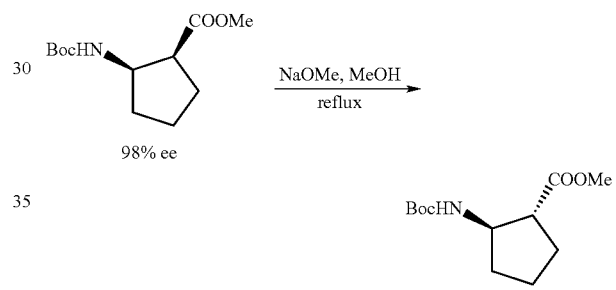

To a solution of cis-(1S, 2R)-2-tert-butoxycarbonylamino-cyclopentanecarboxylic acid ethyl ester 6a (36 mg, 0.15 mmol, 98% ee) in dried MeOH (2 mL) was added NaOMe (40 mg, 0.75 mmol). The mixture was heated to reflux until the starting material totally disappeared according to TLC (24 h). After evaporation of solvent, the residue was directly passed through a silica gel plug to give white crystalline product 6b in 29 mg (80% yield): $[\alpha]^{20}_D$=−40° (c=0.25, CHCl$_3$); $^1$H NMR (CDCl$_3$) 400 MHz δ 4.60 (s, 1H), 4.11 (m, 1H), 3.70 (s, 3H), 2.60 (m, 1H), 2.14 (m, 1H), 1.60–2.10 (m, 5H), 1.45 (s, 9H); MS (ESI): 244 (M$^+$+1); HRMS calcd for C$_{12}$H$_{22}$NO$_4$ 244.1549; found 244.1549. The NMR data is consistent with the reported data.[1] The (−) sign of optical rotation of trans product determined its absolute configuration as (1R, 2R) and thus determined the absolute configuration of the cis hydrogenation product as (1S, 2R).

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A method of preparing enantiomerically enriched cis-cyclic β-acylaminocarbonyl derivative represented by the formula:

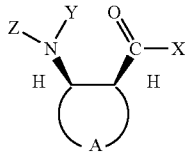

wherein:

X is selected from the group consisting of: alkyl, aryl, substituted alkyl, substituted aryl, heteroaryl, hydrogen, hydroxy, alkoxy, aryloxy, $OCR_2OR$, $OSiR_3$, amino, alkylamino, arylamino, dialkylamino, diarylamino, and alkylarylamino;

Y and Z are independently selected from the group consisting of: hydrogen, alkyl, aryl, substituted alkyl, substituted aryl, heteroaryl, t-BuOCO (BOC), Fmoc peptide protecting group, $PhCH_2OCO$ (CBZ), and COOR, with the proviso that at least one of Y and Z is selected from the group consisting of: t-BuOCO (BOC), Fmoc peptide protecting group, $PhCH_2OCO$ (CBZ), and COOR;

A is selected from the group consisting of: alkylene, substituted alkylene, alkylene of formula $(CH_2)_n$ wherein n is an integer from 1–10, arylene, substituted arylene, heteroarylene, $(CH_2)_l$arylene$(CH_2)_m$, $(CH_2)_l$NR'$(CH_2)_m$, $(CH_2)_l$O$(CH_2)_m$, $(CH_2)_l$S$(CH_2)_m$; $(CH_2)_l$CO$(CH_2)_m$, and $(CH_2)_l$C(=CH_2)(CH_2)_m$;

wherein R' is selected from the group consisting of: hydrogen, alkyl, substituted alkyl, aryl, substituted aryl, acyl, COOR, t-BuOCO (BOC), Fmoc peptide protecting group, and $PhCH_2OCO$ (CBZ);

wherein R is selected from the group consisting of: hydrogen, alkyl, substituted alkyl, aryl, and substituted aryl; and wherein each l and m is independently 0, 1, 2 or 3;

said method comprising the step of:

contacting hydrogen and a cyclic β-(acylamino)acrylate derivative represented by the formula:

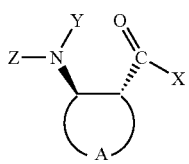

wherein the step of contacting is carried out in the presence of a Ru(II)-chiral phosphine ligand catalyst at a temperature, pressure and for a length of time sufficient to produce the enantiomerically enriched cis-cyclic β-acylaminocarbonyl derivative, wherein X, Y, Z, A, R, R', l, m, and n have the same meaning as before.

2. The method of claim 1, wherein X is selected from the group consisting of: hydroxy, alkoxy, aryloxy, $OCR_2OR$, $OSiR_3$, amino, alkylamino, arylamino, dialkylamino, diarylamino, and alkylarylamino.

3. The method of claim 2, further comprising:
contacting said enantiomerically enriched cis-cyclic β-acylaminocarbonyl derivative and water in the presence of a catalyst under reaction conditions sufficient to convert said enantiomerically enriched cis-cyclic β-acylaminocarbonyl derivative to an enantiomerically enriched cis-cyclic β-aminoacid derivative.

4. The method of claim 3, further comprising:
contacting said enantiomerically enriched cis-cyclic β-aminoacid derivative and a base under reaction conditions sufficient to convert said cis-cyclic β-aminoacid derivative to a trans-cyclic β-aminoacid derivative.

5. The method of claim 1, further comprising:
contacting said enantiomerically enriched cis-cyclic β-acylaminocarbonyl derivative and a base under reaction conditions sufficient to convert said enantiomerically enriched cis-cyclic β-acylaminocarbonyl derivative to an enantiomerically enriched trans-cyclic β-acylaminocarbonyl derivative represented by the formula:

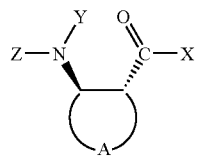

wherein X, Y, Z, A, R, R', l, m, and n have the same meaning as before.

6. The method of claim 5, wherein X is selected from the group consisting of: hydroxy, alkoxy, aryloxy, $OCR_2OR$, $OSiR_3$, amino, alkylamino, arylamino, dialkylamino, diarylamino, and alkylarylamino.

7. The method of claim 6, further comprising:
contacting said enantiomerically enriched trans-cyclic β-acylaminocarbonyl derivative and water in the presence of a catalyst under reaction conditions sufficient to convert said enantiomerically enriched trans-cyclic β-acylaminocarbonyl derivative to an enantiomerically enriched trans-cyclic β-aminoacid derivative.

8. The method of claim 1, wherein the chiral phosphine ligand in said Ru(II)-chiral phosphine ligand catalyst is a chiral monophoshine or bisphosphine compound selected from the group consisting of:
MonoPhos, MOP, ChiraPhos, SkewPhos, BINAP, DIOP, DIOP*, MeO-BIPHEP, Me-BIPHEP, DuPhos, BPE, JosiPhos, Ferrotane, DeguPhos, MeO-BIPHEP, SEGPhos, $H_8$BINAP, BICP, PennPhos, KetalPhos, f-KetalPhos, BINAPHANE, f-BINAPHANE, TangPhos, DuanPhos, BINAPhine, o-BIPHEP, CnTunaPhos (n=1–6), RoPhos, MalPhos, WalPhos, MandyPhos, TaniaPhos, BITIANP, BITIOP, and PhanePhos.

9. The method of claim 8, wherein said Ru(II)-chiral phosphine ligand catalyst is selected from the group consisting of:
$RuHX(L)_2$(diphosphine), $RuX_2(L)_2$(diphosphine), $Ru(aryl)X_2$ (monophosphine)$_2$, $Ru(arene)X_2$(diphosphine), $Ru(aryl)X_2$(diphosphine), $Ru(R"COO)_2$ (diphosphine), $RuCl_2$(=CHR")(monophosphine)$_2$, $[NH_2R"_2][\{RuX(diphosphine)\}_2(\mu\text{-}X)_3]$, RuH(COD)(diphosphine)X, $RuX_2$(diphosphine), and $Ru(methallyl)_2$(diphosphine); wherein R" is selected from the group consisting of: alkyl and aryl; and wherein L is a solvent or alkene, and X is a counteranion selected from the group consisting of: halogen, $BF_4^-$, $B(Ar)_4^-$ wherein Ar is fluorophenyl or 3,5-di-trifluoromethyl-1-phenyl, ClO$_4^-$, SbF$_6^-$, PF$_6^-$, CF$_3$SO$_3^-$, R"COO$^-$ and a mixture thereof.

10. The method of claim 9, wherein said Ru(II)-chiral phosphine ligand catalyst is prepared from a precursor selected from the group consisting of:
Ru(COD)(COT), Ru(COD)(COT)X, RuX$_2$(cymen), Ru(COD)$_n$ wherein n is 2 or 3, RuCl$_2$(COD), Ru(COD)$_2$ X, Ru(ArH)Cl$_2$, and Ru(COD)(methallyl)$_2$.

11. The method of claim 7, wherein said enantiomerically enriched trans-cyclic β-aminoacid derivative is represented by the formula:

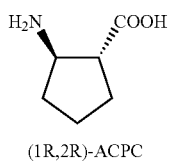

(1R,2R)-ACPC

12. The method of claim 7, wherein said enantiomerically enriched trans-cyclic β-aminoacid derivative is represented by the formula:

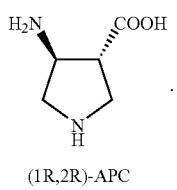

(1R,2R)-APC

13. The method of claim 3, wherein said enantiomerically enriched cis-cyclic β-aminoacid derivative is represented by the formula:

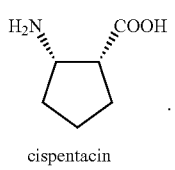

cispentacin

14. A method of preparing enantiomerically enriched cis-hydrogenated acyclic, tetrasubstituted β-acylaminocarbonyl derivative represented by the formula:

YZN—CHR$^1$—CHR$^2$C(O)X wherein:
R$^1$ and R$^2$ independently selected from the group consisting of: alkyl, aryl, substituted alkyl, and substituted aryl;
X is selected from the group consisting of: alkyl, aryl, substituted alkyl, substituted aryl, heteroaryl, hydrogen, hydroxy, alkoxy, aryloxy, OCR$_2$OR, OSiR$_3$, amino, alkylamino, arylamino, dialkylamino, diarylamino, and alkylarylamino;
Y and Z are independently selected from the group consisting of: hydrogen, alkyl, aryl, substituted alkyl, substituted aryl, heteroaryl, t-BuOCO (BOC), Fmoc peptide protecting group, PhCH$_2$OCO (CBZ), and COOR, with the proviso that at least one of Y and Z is selected from the group consisting of: t-BuOCO (BOC), Fmoc peptide protecting group, PhCH$_2$OCO (CBZ), and COOR;
wherein R' is selected from the group consisting of: hydrogen, alkyl, substituted alkyl, aryl, substituted aryl, acyl, COOR, t-BuOCO (BOC), Fmoc peptide protecting group, and PhCH$_2$OCO (CBZ);
wherein R is selected from the group consisting of: hydrogen, alkyl, substituted alkyl, aryl, and substituted aryl; and
wherein each l and m is independently 0, 1, 2 or 3;
said method comprising the step of:
contacting hydrogen and an acyclic, tetrasubstituted β-(acylamino)acrylate derivative represented by the formula:

YZN—CR$^1$=CR$^2$C(O)X wherein the step of contacting is carried out in the presence of a Ru(II)-chiral phosphine ligand catalyst at a temperature, pressure and for a length of time sufficient to produce the enantiomerically enriched cis-hydrogenated acyclic, tetrasubstituted β-acylaminocarbonyl derivative, wherein X, Y, Z, A, R, R', l, m, and n have the same meaning as before.

15. The method of claim 14, wherein X is selected from the group consisting of: hydroxy, alkoxy, aryloxy, OCR$_2$OR, OSiR$_3$, amino, alkylamino, arylamino, dialkylamino, diarylamino, and alkylarylamino.

16. The method of claim 14, further comprising:
contacting said enantiomerically enriched cis-hydrogenated acyclic, tetrasubstituted β-acylaminocarbonyl derivative and water in the presence of a catalyst under reaction conditions sufficient to convert said enantiomerically enriched cis-hydrogenated acyclic, tetrasubstituted β-acylaminocarbonyl derivative to an enantiomerically enriched acyclic β-aminoacid derivative.

17. The method of claim 14, wherein the chiral phosphine ligand in said Ru(II)-chiral phosphine ligand catalyst is a chiral monophoshine or bisphosphine compound selected from the group consisting of:
MonoPhos, MOP, ChiraPhos, SkewPhos, BINAP, DIOP, DIOP*, MeO-BIPHEP, Me-BIPHEP, DuPhos, BPE, JosiPhos, Ferrotane, DeguPhos, MeO-BIPHEP, SEG-Phos, H$_8$BINAP, BICP, PennPhos, KetalPhos, f-Ketal-Phos, BINAPHANE, f-BINAPHANE, TangPhos, DuanPhos, BINAPhine, o-BIPHEP, CnTunaPhos (n=1–6), RoPhos, MalPhos, WalPhos, MandyPhos, TaniaPhos, BITIANP, BITIOP, and PhanePhos.

18. The method of claim 17, wherein said Ru(II)-chiral phosphine ligand catalyst is selected from the group consisting of:
RuHX(L)$_2$(diphosphine), RuX$_2$(L)$_2$(diphosphine), Ru(aryl)X$_2$ (monophosphine)$_2$, Ru(arene)X$_2$(diphosphine), Ru(aryl)X$_2$(diphosphine), Ru(R"COO)$_2$ (diphosphine), RuCl$_2$(=CHR")(monophosphine)$_2$, [NH$_2$R"$_2$][{RuX(diphosphine)}$_2$(μ-X)$_3$], RuH(COD)(diphosphine)X, RuX$_2$(diphosphine), and Ru(methallyl)$_2$(diphosphine); wherein R" is selected from the group consisting of: alkyl and aryl; and wherein L is a solvent or alkene, and X is a counteranion selected from the group consisting of: halogen, BF$_4^-$, B(Ar)$_4^-$ wherein Ar is fluorophenyl or 3,5-di-trifluoromethyl-1-phenyl, ClO$_4^-$, SbF$_6^-$, PF$_6^-$, CF$_3$SO$_3^-$, R"COO$^-$ and a mixture thereof.

* * * * *